United States Patent
Beier et al.

(10) Patent No.: US 10,913,979 B2
(45) Date of Patent: Feb. 9, 2021

(54) DETERMINATION OF MIR-423-5P IN HEART FAILURE

(71) Applicant: HUMMINGBIRD DIAGNOSTICS GMBH, Heidelberg (DE)

(72) Inventors: Markus Beier, Weinheim (DE); Thomas Brefort, Walldorf (DE)

(73) Assignee: HUMMINGBIRD DIAGNOSTICS GMBH, Heidelberg (DE)

( * ) Notice: Subject to any disclaimer, the term of this patent is extended or adjusted under 35 U.S.C. 154(b) by 0 days.

(21) Appl. No.: 15/309,893

(22) PCT Filed: May 20, 2015

(86) PCT No.: PCT/EP2015/061134
§ 371 (c)(1),
(2) Date: Nov. 9, 2016

(87) PCT Pub. No.: WO2015/177222
PCT Pub. Date: Nov. 26, 2015

(65) Prior Publication Data
US 2017/0175192 A1    Jun. 22, 2017

(30) Foreign Application Priority Data
May 23, 2014   (EP) .................... 14169674

(51) Int. Cl.
*C12Q 1/6883* (2018.01)
*C12Q 1/6806* (2018.01)

(52) U.S. Cl.
CPC .......... *C12Q 1/6883* (2013.01); *C12Q 1/6806* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2010/0227319 A1* | 9/2010 | Hoon ................ | G01N 33/5743 435/6.14 |
| 2011/0104785 A1* | 5/2011 | Vaidyanathan .... | C12N 15/1096 435/196 |
| 2012/0115929 A1* | 5/2012 | Creemers ............ | C12N 15/111 514/44 A |
| 2013/0012405 A1 | 1/2013 | Duttagupta et al. | |

FOREIGN PATENT DOCUMENTS

WO    2010/126370    11/2010

OTHER PUBLICATIONS

Cheng et al PLoS One 8(6): e64795, Jun. 7, 2013.*
Fan et al. Indian Heart Journal. Dec. 28, 2012. 65: 12-16.*
Cheng et al,. PLoS One. Jun. 7, 2013. 8(6), Table S3 only, available via URL: <journals.plos.org/plosone/article?id=10.1371/journal.pone.0064795> (Year: 2013).*
International Search Report dated Jul. 1, 2015, in International (PCT) Application No. PCT/EP2015/061134.
Goren et al., "Serum levels of microRNAs in patients with heart failure", European Journal of Heart Failure, vol. 14, Nov. 25, 2011, pp. 147-154.
Tijsen et al., "MiR423-5p as a Circulating Biomarker for Heart Failure", Circulation Research, vol. 106, Apr. 2, 2010, pp. 1035-1039.
Goldraich et al., "Transcoronary gradient of plasma microRNA 423-5p in heart failure: evidence of altered myocardial expression", Biomarkers, vol. 19, No. 2, Feb. 10, 2014, pp. 135-141, XP008176748.

* cited by examiner

*Primary Examiner* — Carla J Myers
(74) *Attorney, Agent, or Firm* — Wenderoth, Lind & Ponack, L.L.P.

(57) ABSTRACT

The present invention relates to methods, kits and uses for diagnosing heart failure using miRNA-biomarker from blood.

16 Claims, 4 Drawing Sheets
Specification includes a Sequence Listing.

| SEQ ID NO: | mirna | RBC | WBC | PCP | PPP | PRP |
|---|---|---|---|---|---|---|
| 1 | hsa-miR-423-5p | 412 | 407 | 329 | 244 | 1252 |

Figure 3

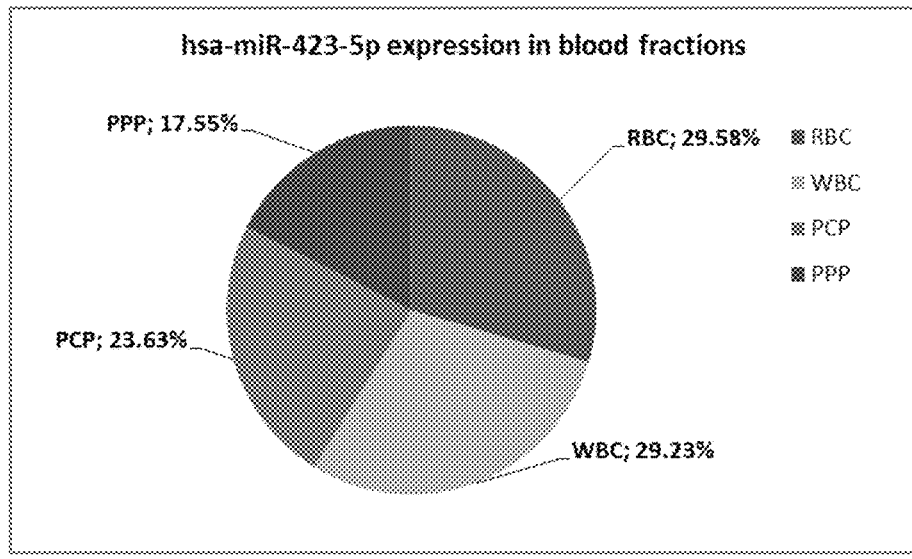

Figure 4

| SEQ ID NO: | miRNA | HealthyControl, median g1 | Heart Failure, median g2 |
|---|---|---|---|
| 1 | hsa-miR-423-5p | 2297 | 3994 |

Figure 5

| A | B | C | D | E |
|---|---|---|---|---|
| Seq ID NO: | Stem-Loop Reverse Primer | Forward Primer | Reverse Primer | Dual-Labeled Probe |
| 1 | X-AAAGTCTC | Y-TGAGGGGCAGAGAGCGA (SEQ ID NO:2) | Z | 56-FAM-P-AAAGTCTC-3IABLFQ | with X =5'-CTCAACTGGTGTCGTGGAGTCGGCAATTCAGTTGAG (SEQ ID NO:3)

with Y =5'-ACACTCCAGCTGGG (SEQ ID NO:4)

with Z =5'-CTCAACTGGTGTCGTGGAGT (SEQ ID NO:5)

with P =5'-TTCAGTTGAG (SEQ ID NO:6)

with 56-FAM =5' 6-FAM (Fluorescein)

with 3IABLFQ=Iowa black fluorescein quencher

Figure 6

| A | B | C |
|---|---|---|
| Seq ID NO: | Forward Primer (SEQ ID NO:7) | Reverse Primer (SEQ ID NO:8) |
| 1 | GGGCAGAGAGCGAGAC | GGTCCAGTTTTTTTTTTTTTTTAAAGTC |

Figure 7

| DNA-Fragment add to 3'-end of miRNA | Analysis Technique | Reference |
|---|---|---|
| dC utilizing T4 RNA ligase | microarray | PMID:17105992, Wang, H., et.al., RNA. 151–159 (2007) |
| (bio-dATP)n or (bio-dCTP)n or (bio-dGATP)n or (bio-dAUTP)n with n=1 to 12 utilizing Klenow-Fragment of DNA polymerase I | microarray | PMID:1878666, Vorwerk, S. et al. N. Biotechnol. 25, 142–9 (2008). |
| adding of a complex DNA-tag by ligation | microarray | PMID:21813625, Wyman S.K. et.al., Genome Res. 2011, 21(9):1450-61. |
| TGGAATTCTCGGGTGCCAAGG (SEQ ID NO:9) | Next Generation Sequencing | Illumina website |
| 5' P-UCGUAUGCCGUCUUCUGCUUGUidT (SEQ ID NO:10) | Next Generation Sequencing | Illumina website |
| AMP-5'p-5'p-CTGTAGGCACCATCAATdi-deoxyC (SEQ ID NO:11) | Next Generation Sequencing | Illumina website |
| AMP-5'p-5'p-ATCTCGTATGCCGTCTTCTGCTTGdi-deoxyC (SEQ ID NO:12) | Next Generation Sequencing | Illumina website |

Figure 8

| A | B | C | D | E |
|---|---|---|---|---|
| 3' RNA Adapter | 5' RNA Adapter | RT Primer | Small RNA PCR Primer 1 | Small RNA PCR Primer 2 |
| P-UCGUAUGCCGUCUUCUGCUUGUidT (SEQ ID NO:10) | GUUCAGAGUUCUACAGUCCGACGAUC (SEQ ID NO: 13) | CAAGCAGAAGACGGCATACGA (SEQ ID NO:14) | CAAGCAGAAGACGGCATACGA (SEQ ID NO:14) | AATGATACGGCGACCACCGACAGGTTCAGAGTTCTACAGTCCGA (SEQ ID NO:17) |
| 5' /5rApp/ATCTCGTATGCCGTCTTCTGCTTG/3ddC/ (SEQ ID NO:12) | GUUCAGAGUUCUACAGUCCGACGAUC (SEQ ID NO: 13) | CAAGCAGAAGACGGCATACGA (SEQ ID NO:14) | CAAGCAGAAGACGGCATACGA (SEQ ID NO:14) | AATGATACGGCGACCACCGACAGGTTCAGAGTTCTACAGTCCGA (SEQ ID NO:17) |
| 5' TGGAATTCTCGGGTGCCAAGG (SEQ ID NO:9) | 5' GUUCAGAGUUCUACAGUCCGACGAUC (SEQ ID NO: 13) | 5' GCCTTGGCACCCGAGAATTCCA (SEQ ID NO:15) | CAAGCAGAAGACGGCATACGAGATCGTGATGTGACTGGAGTTCCTTGCACCCGAGAATTCCA 9SEQ ID NO:16) | AATGATACGGCGACCACCGAGATCTACACGTTCAGAGTTCTACAGTCCGA (SEQ ID NO:18) | with :

(A) 3' RNA Adapter = DNA fragment added to 3'end of miRNA via ligation reaction (B) 5' RNA Adapter = DNA fragment added to 5'end of miRNA via ligation reaction (C) RT Primer = primer for reverse-transcribing said RNA-DNA hybrid to cDNA (D) Small RNA PCR Primer 1 = universal forward primer for amplifying the cDNAs (E) Small RNA PCR Primer 2 = universal reverse primer for amplifying the cDNAs

DETERMINATION OF MIR-423-5P IN HEART FAILURE

TECHNICAL FIELD OF THE INVENTION

The present invention relates to methods, use and kits for the determination of hsa-miR.423-5p in heart failure (HF).

BACKGROUND OF THE INVENTION

Today, biomarkers play a key role in early diagnosis, risk stratification, and therapeutic management of various diseases. MicroRNAs (miRNAs) are a new class of biomarkers. So far, miRNAs have been extensively studied in tissue material where it was found that miRNAs are expressed in a highly tissue-specific manner. Since recently it is known that miRNAs are not only present in tissues but also in body fluid samples, including blood. Nevertheless, the mechanism why miRNAs are found in blood, especially in the cellular blood fraction (blood cells of subfractions thereof) or in the extra-cellular fraction (serum/plasma), or their function in these blood fractions is not understood yet.

It is known that hsa-miR-423-5p may be employed as a biomarker for diagnosis of heart failure (Tijsen A J et. al, Circ Res. 2010 Apr. 2; 106(6):1035-9, Tijsen A J et, al. Cardiovasc Res. 2012 Mar. 15; 93(4):573-82, Tijsen A J et. al. Am J Physiol Heart Circ Physiol. 2012 Nov. 1; 303(9): H1085-95, WO2010126370). In these studies hsa-miR-423-5p was determined from plasma samples and it was shown that hsa-miR-423-5p is upregulted in heart failure patients as compared to healthy controls. One further study found hsa-miR-423-5p upregulated in in serum of heart failure patients as compared to healthy controls (Goren et. al Eur J Heart Fail. 2012 February; 14(2):147-54). But there are also other studies wherein the authors were not able to reproduce these findings, namely that hsa-miR-423-5p qualifies as a biomarker for heart failure (Tutarel O et. al, Int J Cardiol. 2013 Jul. 15; 167(1):63-6, Kumarswamy R et. al Circ Res. 2010 May 14; 106(9):e8; author reply e9; Bauters C et. al. Int J Cardiol. 2013 Oct. 3; 168(3):1837-40).

Surprisingly, the inventors of the present invention found that hsa-miR-423-5p is not only present in plasma or serum samples of heart failure (HF) patients, but also in different blood cell fractions derived from a whole blood sample. They surprisingly found that hsa-miR-423-5p is expressed not only in the extra-cellular fraction (serum/plasma), but also in the cellular fraction, namely in red blood cells, white blood cells and platelets (see FIGS. 2, 3). This directly influences the potential use of hsa-miR-423-5p as a biomarker from plasma and serum in the diagnosis of heart failure since contaminating blood cells will contribute to the overall level of hsa-miR-423-5p determined in plasma or serum samples. This contaminating effect of hsa-miR-423-5p molecules originating from blood cells is severe, since the level of hsa-miR-423-5p is much higher in blood cells (red blood cells, white blood cell, platelets) when compared to the level of hsa-miR-423-5p in plasma or serum samples (see FIGS. 2, 3).

The inventors of the present invention found that by strictly avoiding contamination of blood cells in the preparation of serum and plasma samples, superior and reliable result for hsa-miR-423-5p could be achieved in the use of hsa-miR-423-5p in the diagnosis of heart failure. Especially when plasma samples are employed in the diagnosis of heart failure using hsa-miR-423-5p it is of utmost importance to exclude contaminating platelets in the sample preparation procedures due to high expression of hsa-miR-423-5p in platelets and the high number of platelets in blood samples. The inventors of the present invention further found that when using serum and plasma samples further contamination by blood cells may originate from blood cell lysis arising when the extra-cellular fraction (plasma, serum) is not separated from the cellular fraction (blood cells, namely red blood cells, white blood cells and platelets) in due time.

The inventors of the present invention developed robust and reliable methods that allow the determination of hsa-miR-423-5p from the extra-cellular blood fraction (plasma, serum) which which allow the use of hsa-miR-423-5p as a biomarker in the diagnosis of heart failure. By following these robust and reliable methods, contamination by hsa-miR-423-5p originating from blood cells or platelets can be prevented and and as a result higher diagnostic power (specificity, sensitivity) can be achieved in the diagnosis of heart failure.

SUMMARY OF THE INVENTION

In a first aspect, the invention provides for a method for diagnosing heart failure by determining an expression profile of a set of miRNAs comprising at least hsa-miR-423-5p from a plasma sample of a subject, wherein said plasma sample is free or substantially free of blood cells or platelets (and microvesicles).

In a second aspect, the invention provides for a kit for diagnosing heart failure, comprising:
 (a) means for determining an expression profile of a set (of miRNAs) comprising at least hsa-miR-423-5p in platelet-poor plasma sample (a plasma sample free or substantially free of blood cells or platelets)
 (b) a reference
 (c) optionally a data carrier
 (d) optionally means for preparing a platelet-poor plasma from a whole blood sample
 (e) optionally a whole blood collection tube
 wherein the reference is derived from expression profiles determined from of a set of miRNAs comprising at least hsa-miR-423-5p in a platelet-poor plasma sample (a plasma sample free or substantially free of blood cells or platelets) of at least 2 subjects with 2 clinical conditions from which at least one is heart failure.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual, 2$^{nd}$ Edition*, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. The miRNAs regulate gene expression and are encoded by genes from whose DNA they are transcribed, but miRNAs are not translated into protein (i.e. miRNAs are non-coding RNAs). The terms "microRNA*" or "miRNA*" refer to miRNA molecules derived from the passenger strand upon processing. In the context of the present invention, the terms "miRNA" and "miRNA*" are interchangeable used. The miRBase (www.mirbase.org) is a well established repository and searchable database of published miRNA sequences and annotation. Because of the conservation of miRNAs among species, for example between humans and other mammals, e.g. animals such as mice, monkey or rat, a human miRNA may also be suitable for detecting the respective miRNA orthologue(s) in another species, e.g. in another mammal, e.g. in an animal such as mouse or rat or vice versa.

The term "platelet" as used in the context of the present invention refers to the smallest type of blood cells, also known as "thrombocytes", which are released into the blood stream from bone marrow megakaryocytes.

The term "whole blood sample", as used in the context of the present invention, refers to a blood sample originating from a subject containing all blood fractions, including both the cellular (red blood cells, white blood cells, platelets) and the extra-cellar blood fractions (serum, plasma). The "whole blood sample" may be derived by removing blood from a subject by conventional blood collecting techniques, but may also be provided by using previously isolated and/or stored blood samples. Preferably, the whole blood sample from a subject (e.g. human or animal) has a volume of between 0.1 and 40 ml, more preferably of between 0.5 and 20 ml, more preferably between 1 and 15 ml and most preferably between 2 and 10 ml, i.e. 0.1, 0.2, 0.3, 0.4, 0.5, 0.6, 0.7, 0.8, 0.9, 1, 2, 2.5, 3, 4, 5, 6, 7, 8, 9, 10, 51, 12, 13, 14, 15, 16, 17, 18, 19, 20, 21, 22, 23, 24, 25, 26, 27, 28, 29, 30, 31, 32, 33, 34, 35, 36, 37, 38, 39 or 40 ml.

The term "platelet-rich-plasma" (PRP) as used herein relates to a blood plasma sample with high number of blood cells, preferably with a high number of platelets.

The term "platelet-poor-plasma" (PPP) as used herein relates to blood plasma sample with very low number of blood cells (<10×10$^3$/μL), preferably with a very low number of platelets (<10×10$^3$/μL). Therefore, a platelet-poor-plasma sample is free of or substantially free of blood cells, preferably a platelet-poor-plasma sample is substantially free of platelets. A platelet-poor-plasma sample is obtained from a platelet-rich-plasma sample by depletion or removal of the blood cells, preferably by removal of the platelets. This depletion or removal may be e.g. performed by centrifugation of the PRP-sample, preferably at high relative centrifugal force or high rotational speed, wherein the remaining blood cells or platelets sediment at the bottom of the tube as a pellet and the PPP represents the supernatant that is now free of or substantially free of blood cells or platelets.

According to the present invention it is of utmost importance for employing hsa-miR-423-5p (SEQ ID NO: 1) as a biomarker for heart failure, that any contaminating hsa-miR-423-5p molecules that do originate from expression in blood cells, preferably that originate from expression in platelets are removed or depleted from the test sample before the expression of hsa-miR-423-5p is determined according to the method of the present invention. Otherwise, the determination of the expression of hsa-miR-423-5p is confounded by contaminating hsa-miR-423-5p molecules originating from blood cells, since hsa-miR-423-5p is highly expressed in blood cells including platelets, red blood cells or white blood cells (see FIGS. 2, 3). Any confounding contribution of hsa-miR-423-5p expression originating from blood cells or platelets will increase the expression of hsa-miR-423-5p in the test sample by mistake, since upregulation of hsa-miR-423-5p is determinative for diagnosis of heart failure. Therefore, any confounding contribution of hsa-miR-423-5p expression originating from blood cells or platelets will lead to overdiagnosis of heart failure.

The inventors of the present invention surprisingly found that hsa-miR-423-5p is not only present in the extracellular fraction of blood (serum/plasma), but also in the cellular fraction of blood (see FIG. 4). As the expression of hsa-miR-423-5p in blood cells, especially in platelets, is comparably high, it has to be warranted that the test sample is free or substantially free of confounding blood cells or platelets when determining the expression of hsa-miR-423-5p in the test sample in order not to overdiagnose heart failure by mistake. It is important not to use the PRP-fraction for the determination of expression hsa-miR-423-5p for diagnosing heart failure, because this fraction contains a high number of blood cells including platelets which significantly contribute to the overall expression of hsa-miR-423-5p (see FIGS. 2, 3). Therefore, safeguarding that the plasma test sample is not contaminated by blood cells or platelets, allows to improve the diagnosis of heart failure.

The term "total RNA" as used herein relates to the RNA isolated from a whole blood sample or a plasma fraction thereof, preferably in the diagnosis of heart failure employing hsa-miR423-5p the total RNA is isolated from a plasma sample that is free or substantially free of blood cells or platelets. The total RNA, comprising the miRNA-fraction or comprising a miRNA-enriched fraction, is e.g. obtained by RNA isolation (extraction) e.g. by phenol/chloroform extraction and/or separation based techniques (e.g. glass fibre filter column, silica-membrane column). Examples of kits for RNA isolation and purification include the miRNeasy Kits (Qiagen), PAXgene™ Blood miRNA Kit (Qiagen), mirVana PARIS Kit (Life Technologies), PARIS Kit (Life Technologies), Tempus Spin RNA Isolation Kit (Life Technologies). Preferably, the total RNA according to the present invention contains the miRNA-fraction or contains a miRNA-enriched fraction.

The term "expression profile" as used in the context of the present invention, represents a measure that correlates with the miRNA expression (level) in said sample. By determining the miRNA expression profile, each miRNA is represented by a numerical value. The higher the value of an individual miRNA, the higher is the expression level of said miRNA, or the lower the value of an individual miRNA, the lower is the expression level of said miRNA. The expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/ 454 GS FLX), flow cytometry (e.g. LUMINEX, Milipore Guava) and the like, that allow the determination of a miRNA expression profile in a subject and comparison between samples. The sample material measured by the aforementioned means may be total RNA, labeled total RNA, amplified total RNA, cDNA, labeled cDNA, amplified cDNA, miRNA, labeled miRNA, amplified miRNA or any derivatives that may be generated from the aforementioned RNA/DNA species. The "expression profile", as used herein, relates to a collection of expression (levels) of at least one miRNAs, preferably of least 1, 2, 3, 4, 5, 6, 7, 8, 9, 10, 11, 12, 13 or more miRNAs, preferably comprising at least hsa-miR-423-5p (SEQ ID NO:1).

The term "determining an expression profile" as used herein, relates to the determination of the expression profile of set comprising at least hsa-miR-423-5p (SEQ ID NO:1). By doing so, the determination of the expression profile is a measure that directly or indirectly correlates with the levels of said at least one miRNA present in said plasma fraction (plasma free or substantially free of blood cells or platelets) derived from the whole blood sample. Herein, all steps or transformations required to bring the isolated total RNA (comprising said miRNAs, comprising hsa-miR-423-5p) into a form which allows to determine the expression profile by any convenient means (e.g. nucleic acid hybridisation, nucleic acid amplification, polymerase extension, mass spectroscopy, flow cytometry, sequencing) and which are known to the person skilled in the art, are included, e.g. RNA- or miRNA-isolation, RNA- or miRNA-enrichment, RNA- or miRNA-purification, RNA- or miRNA-labeling, polymerase extension of RNA or miRNA, ligation of RNA or miRNA, reverse-transcription of RNA or miRNA into cDNA, amplification of the cDNA, labelling of cDNA).

The term "nucleic acid hybridization", as used herein, relates to a means for determining an expression profile. The nucleic acid hybridization may be performed using a microarray/biochip or in situ hybridization. For nucleic acid hybridization, for example, the polynucleotides (probes) with complementarity to the corresponding miRNAs to be detected are e.g. attached to a solid phase to generate a microarray/biochip. Said microarray/biochip is then incubated with a sample containing the miRNA(s), which may be labelled or unlabelled. Quantification of the expression level of the miRNAs may then be carried out e.g. by direct read out of said label or by additional manipulations, e.g. by use of an enzymatic reaction. Alternatively, the polynucleotides which are at least partially complementary to a set of miRNAs comprising at least SEQ ID NO: 1 (or a species derived thereof, e.g. a cDNA-species) are contacted with said sample containing said miRNA(s) (or a species that is derived from said miRNA(s), e.g. a cDNA-species) in solution to hybridize. Afterwards, the hybridized duplexes are pulled down to the surface and successfully captured miRNAs are quantitatively determined (e.g. FlexmiR-assay, FlexmiR v2 detection assays from Luminex, Fireplex assay from Firefly Bioworks).

The term "nucleic acid amplification", as used herein, relates to a means for determining an expression profile. Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 10 miRNAs), whereas high-throughput RT-PCR technologies (e.g. OpenArray from Applied Biosystems, Smart-PCR from Wafergen, Biomark System from Fluidigm) are also able to measure large sets (e.g a set of 5, 10, 20, 30, 50, 80, 100, 200 or more) to all known miRNAs in a high parallel fashion. The aforesaid real time polymerase chain reaction (RT-PCR) may include the following steps: (i) extracting/isolating the total RNA from a plasma fraction (a plasma fraction free or substantially free of blood cells or platelets) derived from the whole blood sample collected in a whole blood collection tube (ii) obtaining cDNA samples by RNA reverse transcription (RT) reaction using universal or miRNA-specific primers; (iii) optionally pre-amplifying the cDNA of step (ii) via polymerase chain reaction (PCR), (iv) amplifying the optionally pre-amplified cDNA via polymerase chain reaction (PCR), thereby monitoring the amplification through a previously added fluorescent reporter dye (e.g. SYBR Green) or fluorescent reporter probe (e.g. Taqman probe), and (v) detecting the miRNA(s) level in the sample from the monitoring in step (iv). In Step (i) the isolation and/or extraction of RNA may be omitted in cases where the RT-PCR is conducted directly from the miRNA-containing sample. Kits for determining a miRNA expression profile by real time polymerase chain reaction (RT-PCR) are e.g. from Life Technologies, Applied Biosystems, Ambion, Roche, Qiagen, Invitrogen, SABiosciences, Exiqon. Examples of primers and adapters employed in determining the expression profile of hsa-miR-423-5p by amplification such as qRT-PCR are depicted in FIG. 5 or FIG. 6.

The term "sequencing", as used herein, relates to a means for determining an expression profile, including conventional (Maxam-Gilbert, Sanger) sequencing technology, Pyrosequencing or next generation sequencing technology (e.g. ABI SOLID, Illumina Hiseq, Gnubio, Pacific Biosystems, 454) or any other sequencing technology, capable of determination of the expression profile of set of miRNAs comprising at least hsa-miR-423-5p. Examples of primers and adapters employed in determining the expression profile of hsa-miR-423-5p by sequencing such as next generation sequencing are depicted in FIG. 8.

The term "reference" as used in the context of the present invention refers to a reference to which the expression profile of a test sample of a subject affected by HF or suspected to be affected by HF is compared in the course of non-invasive diagnosis of HF. Herein, both the expression profile of the subject (affected by HF or suspected to be affected by HF) to be tested as well as the reference, are determined from the same miRNAs and the same sample type (collected and worked up in the same way), preferably they are determined from plasma fraction derived from the whole blood sample collected in whole blood collection tubes that is free or substantially free of blood cells or platelets. The reference may be a reference expression profile obtained from determining one or more expression profiles of a set of miRNAs comprising at least hsa-miR-423-5p from a plasma sample that is free or substantially free of blood cells or platelets derived from the whole blood sample collected in whole blood collection tubes in one or more reference subjects. Furthermore, the reference may be an algorithm, a mathematical function or a score that was developed from such aforementioned reference expression profiles. The term "heart failure" (HF), relates to a condition when the heart is unable to provide sufficient pump action to maintain blood flow to meet the needs of the body. Heart Failure is diagnosed by patient physical examination and confirmed with echocardiography. Blood tests (e.g. NT-proBNP) help to determine the cause. Treatment depends on severity and cause of heart failure. In a chronic patient already in a stable situation, treatment commonly consists of lifestyle measures such as smoking cessation, light exercise, dietary changes, and medications. Sometimes, depending on etiology, Heart Failure is treated with implanted devices (pacemakers or ventricular assist devices) and occasionally a heart transplant is required.

The term "diagnosing" as used in the context of the present invention refers to the process of determining a possible disease (e.g. Heart Failure) or disorder or a certain component of a disease (e.g. an inflammatory component of a disease) and therefore is a process attempting to define the (clinical) condition of a subject. The determination of the expression profile of at least one miRNA according to the present invention correlates with the (clinical) condition of said subject. Preferably, the diagnosis comprises (i) determining the occurrence/presence of the disease (or of a component of a disease), especially in an (very) early phase of the disease (ii) monitoring the course or progression of the disease, (iii) staging of the disease, (iv) measuring the response of a patient affected with the disease to therapeutic intervention, (v) monitoring the efficacy of a therapeutic intervention and/or (vi) segmentation of a subject suffering from the disease.

An exemplarily approach to determine expression profiles in HF of a set comprising at least SEQ ID NO: 1 in a plasma sample free or substantially free of blood cells or platelets is summarized below:

Step 1: Providing a whole blood sample of a subject: Whole blood is drawn from a subject (affected by HF or suspected to be affected by HF) into a EDTA-tube (Sarstedt, S-Monovette EDTA-$K_2$, 9 ml); drawing of 9 ml of whole blood into EDTA-tube tube is sufficient for the downstream analyses. The tube should be carefully inverted to ensure that the reagents contained are thoroughly mixed with the blood. The tube should not kept at room temperature for longer than 4 hours, preferably no longer than 1 hour, more preferably not longer than 30 min before centrifugation. (see FIG. 1)

Step 2: Depletion or removal of the blood cells or platelets: The collected whole blood sample is centrifuged with soft spin (170 g, 15 min) to separate the blood cell fractions. After centrifugation the whole blood sample is separated into Platelet-Rich-Plasma (PRP, top-fraction), buffy coat (white blood cells; middle-fraction, interphase) and red blood cells (bottom fraction). From this the platelet-comprising fraction, namely the Platelet-Rich-Plasma is collected. Subjecting the PRP to a second hard spin centrifugation (5000 g, 3 min), remaining blood cells or platelets are pelleted out of the PRP to yield platelet-concentrate (as pellet) and platelet-poor-plasma (PPP) as supernatant. (see FIG. 1)

Step 3: Isolation of the total RNA from said platelet-comprising fraction derived from the whole blood sample: The total RNA is isolated from the PPP-fraction obtained in Step 2, namely from Platelet-Poor-Plasma using suitable kits (e.g. miRNeasy kit) and/or purification methods.

Step 4: Determining an expression profile of a set comprising at least hsa-miR-423-5p (SEQ ID NO:1) from the total RNA isolated: From the total RNA isolated the expression profile of a set comprising at least hsa-miR-423-5p (SEQ ID NO:1) is measured using experimental techniques. These techniques include but are not limited to nucleic acid hybridisation based approaches, nucleic acid amplification methods (PCR, RT-PCR, qPCR), sequencing, next generation sequencing, flow cytometry and/or mass spectroscopy. In a preferred embodiment, it may be required in Step 4 that the total RNA is reverse-transcribed into cDNA and optionally be amplified before the expression profile is determined.

In order to make use of the determined expression profiles in a method for diagnosing HF, further steps are performed:

Step 5: Comparing said expression profile to a reference: The expression profile obtained in Step 4) is compared to a reference. The reference may be e.g. a reference expression profile, obtained from determining the expression profile of said set of miRNAs comprising at least hsa-miR-423-5p (SEQ ID NO:1) in a plasma-fraction (free or substantially free of blood cells or platelets) derived from the whole blood sample collected in the same type of whole blood collection tube as in Step 1 (here: collected in a Kalium-EDTA-tube; Sarstedt S-Monovette) in one or more reference subjects or the reference may be an algorithm, a mathematical function or a score that was developed from such a reference expression profile.

Step 6: Identifying if said subject is affected by a HF related condition: The comparison to the reference then allows to identify if said subject is affected or not affected by HF.

Step 7: Optionally administering said affected subject to therapy: Optionally, said subject, that was identified to be affected by HF is administered to therapy, e.g. by treating the subject with drugs suited for therapy of HF. Or alternatively subjecting said subject, if certain thresholds for monitoring the progression of HF are reached, to an altered therapeutic scheme, wherein said altered therapeutic scheme may be an increased or decreased therapeutic scheme with administering appropriate drugs at increased or decreased dosage.

In a first aspect, the present invention relates to a method for diagnosing heart failure by determining an expression profile of a set of miRNAs comprising at least hsa-miR-423-5p (SEQ ID NO:1) from a plasma sample of a subject, wherein said plasma sample is free or substantially free of blood cells or platelets. Preferably the plasma (test) sample according to the present invention is free or substantially free of platelets (before from said plasma (test) sample the total RNA is isolated, from which the determination of the expression profile of a set of miRNAs comprising at least hsa-miR-423-5p (SEQ ID NO:1) is started. More preferably the plasma (test) sample according to the present invention is free or substantially free of hsa-miR-423-5p molecules originating from blood cells or platelets (before from said plasma (test) sample the total RNA is solated, from which the determination of the expression profile of a set of miRNAs comprising at least hsa-miR-423-5p (SEQ ID NO:1) is started.

Preferably the plasma-(test) sample is a platelet-poor-plasma sample. More preferably, the plasma-(test) sample is a plasma sample that is free or substantially free of blood cells or platelets.

In a second aspect, the invention relates to a kit for diagnosing heart failure.

Said kit is for use in the method according to the first aspect of the invention.

The kit for use in the method according to the first aspect of the invention comprises:
(a) means for determining an expression profile of a set of miRNAs comprising at least hsa-miR-423-5p in plasma sample that is free or substantially free of blood cells or platelets
(b) a reference
(c) optionally a data carrier
(d) optionally means for preparing a platelet-poor plasma from a whole blood sample
(e) optionally a whole blood collection tube
wherein the reference is derived from expression profiles determined from of a set of miRNAs comprising at least hsa-miR-423-5p in plasma sample that is free or substantially free of blood cells or platelets of at least 2 subjects with 2 clinical conditions from which at least one is Heart Failure.

The plasma sample according to the second aspect of the invention is free or substantially free of blood cells or platelets. Preferably, the plasma sample is a platelet-poor plasma sample.

In summary, the present invention is composed of the following items:
1. Method for diagnosing Heart Failure by determining an expression profile of a set of miRNAs comprising at least hsa-miR-423-5p from a plasma sample of a subject, wherein said plasma sample is free of or substantially free of/depleted of blood cells (and microvesicles).
2. The method according to item 1, wherein the plasma sample is free of or substantially free of/depleted of red blood cells, white blood cells and platelets (and microvesicles).
3. The method according to any of the item 1 to 2, wherein the plasma sample is free of or substantially free of hsa-miR-423-5p expressed in red blood cells, white blood cells and platelets.
4. The method according to any of the item 1 to 3, wherein the plasma sample is a platelet-poor-plasma sample.
5. The method according to any of the items 1 to 4, wherein the plasma sample was prepared by at least 2 centrifugation steps.
6. The method according to any of the items 1 to 5, comprising the steps:
(a) Providing a whole blood sample of a subject
(b) Preparing a platelet-poor plasma sample from said whole blood sample
(c) Isolation of the total RNA from said platelet-poor plasma sample
(d) Determining an expression profile of a set comprising at least hsa-miR-423-5p from the total RNA isolated
(e) Comparing said expression profile to a reference
(f) Identifying if said subject is affected by Heart Failure
(g) Optionally administering said affected subject to therapy
7. The method according to any of the items 4, 5 or 6, wherein the preparation of the platelet-poor-plasma sample comprises the steps:
(i.) Centrifugation of the whole blood sample to result in separation of red blood cell fraction, buffy coat and platelet-rich plasma
(ii.) Centrifugation of the platelet-rich plasma obtained in step (i) to result in separation of a pellet and platelet-poor plasma.
8. The method according to item 7, wherein the centrifugation in step (i) is carried out with higher centrifugation speed as the centrifugation in step (ii).
9. The method according to any of the items 1 to 8, wherein the determining of the expression profile in step (d) comprises the steps
a. Transcribing the total RNA into cDNA
b. Optionally amplifying said cDNA
c. Determining the expression profile of a set comprising at least hsa-miR-423-5p from the cDNA-transcripts of step (a) or (b)
10. A kit for use in the method according to any of the items 1 to 8, comprising:
(a) means for determining an expression profile of a set of miRNAs comprising at least hsa-miR-423-5p in plasma sample that is free of or substantially free of blood cells or platelets
(b) a reference
(c) optionally a data carrier
(d) optionally means for preparing a platelet-poor plasma from a whole blood sample
(e) optionally a whole blood collection tube
wherein the reference is derived from expression profiles determined from of a set comprising at least hsa-miR-423-5p in in plasma sample that is free of or substantially free of blood cells or platelets of at least 2 subjects with 2 clinical conditions from which at least one is Heart Failure.
11. The kit according to item 10, wherein the plasma sample is a platelet-poor-plasma sample.
12. The kit according to any of the items 10 to 11, wherein the means for determining an expression profile comprise primers or adapters listed in FIGS. 5 to 8.
13. The kit according to item 12, wherein said means are for determining an expression profile by qRT-PCR, comprising primers or adapters listed in FIG. 5 or FIG. 6.
14. The kit according to item 12, wherein said means are for determining an expression profile by next generation sequencing, comprising primers or adapters listed in FIG. 8.
15. The method according to any of the items 1 to 9 or the kit according to any of the items 10 to 14, wherein said plasma sample comprises less than 10,000 blood cells per microliter, preferably wherein said plasma sample comprises less than 10,000 platelets per microliter.

BRIEF DESCRIPTION OF THE DRAWINGS

FIG. 3: Relative expression of hsa-miR-423-5p (SEQ ID NO: 1) in percent in RBC (red blood cells), WBC (white blood cells), PCP (Platelet concentrated plasma), PPP (platelet-poor-plasma), as described in FIG. 2. Normalization by the cumulative expression of hsa-miR-423-5p in RBC+WBC+PCP+PPP.

FIG. 4: HEART FAILURE (HF): expression of hsa-miR-423-5p in blood cells (derived from whole blood collected in PAXgene blood RNA-tubes comprising red blood cells, white blood cells and platelets) in healthy subjects (g1) and subjects diagnosed with heart failure (g2). With "SEQ ID NO:"=sequence identification number, "miRNA"=identifier of the miRNA according to miRBase (see the miRBase website), "Healthy Control median g1"=median intensity (expression level) obtained from microarray analysis for healthy control subjects in counts/sec; "HF median g2"="=median intensity (expression level) obtained from microarray analysis for HF subjects in counts/sec.

FIG. 5: miRNA-specific DNA-primers (column B) used for reverse transcription (RT) of hsa-miR-423-5p (SEQ ID NO: 1) to non-naturally occurring cDNA; miRNA-specific forward and universal reverse primers (column C, D) for quantification and optionally amplification of hsa-miR-423-5p (SEQ ID NO: 1) employed for determining of an expression profile representative for HF; dual-labeled hydrolysis probes (Taqman-probes, column E) utilized for quantifying of hsa-miR-423-5p (SEQ ID NO: 1) by real-time PCR.

FIG. 6: miRNA-specific forward primer (column B) and partially universal reverse primer (column C) for quantification and optionally amplification of cDNA-transcripts of hsa-miR-423-5p (SEQ ID NO: 1) employed for determining of an expression profile of hsa-miR-423-5p (SEQ ID NO: 1) representative for HF.

FIG. 7: DNA-fragments added to the 3'-end of hsa-miR-423-5p (SEQ ID NO: 1) employed for determining of an expression profile of hsa-miR-423-5p (SEQ ID NO: 1) representative for HF, thereby forming non-naturally occurring RNA-DNA hybrids.

FIG. 8: Adapters, RT-primers and PCR-primers utilized for next generation sequencing (Illumina small RNA-seq) of hsa-miR-423-5p (SEQ ID NO: 1) employed for determining of an expression profile of hsa-miR-423-5p (SEQ ID NO: 1) representative for HF: universal 3' RNA Adapters (column A) ligated to the 3'-end of hsa-miR-423-5p (SEQ ID NO: 1); universal 5' RNA Adapter (column B) ligated to the 5'-end of hsa-miR-423-5p (SEQ ID NO: 1); universal reverse transcription (RT)-Primers (column C) for reverse-transcribing the 3'- and 5'-adapter ligated miRNAs into (non-naturally occurring) cDNA; Small RNA PCR Primer 1=universal forward (column D) and Small RNA PCR Primer 2=universal reverse (PCR) primers (column E) for amplifying the 3'- and 5'-adapter ligated and reverse-transcribed cDNAs of hsa-miR-423-5p (SEQ ID NO: 1).

EXAMPLES

Figures 1, 2:
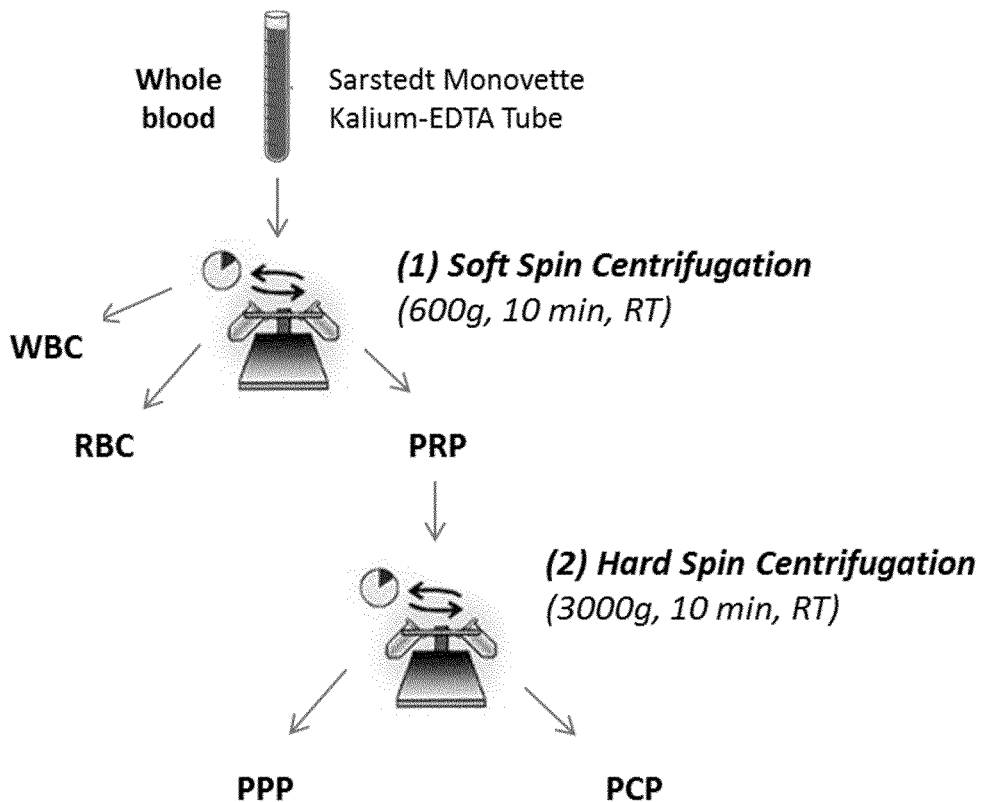
FIG. 1: Route for preparing platelet-poor-plasma (PPP). A whole blood sample is subjected to a soft (slow) spin centrifugation (600 g, 10 min, RT), from which (besides RBCs, WBCs) the platelet-rich-plasma (PRP) fraction can be obtained. This PRP-fraction is not free or substantially free of blood cells or platelets. In order to obtain a plasma fraction, that is free or substantially free of blood cells or platelets, the PRP is subjected to a second hard (fast) centrifugation step (3000 g, 10 min, RT). From this second centrifugation the platelet-poor-plasma (PPP) fraction can be obtained, which is free or substantially free of blood cells or platelets.
FIG. 2: Relative expression of hsa-miR-423-5p (SEQ ID NO: 1) in different blood fractions from healthy controls with RBC (red blood cells), WBC (white blood cells), PCP (Platelet concentrated plasma), PPP (platelet-poor-plasma), PRP (platelet-rich-plasma); expression levels of each of the different blood fraction were obtained by microarray (Agilent) analysis; in order to be able to compare the expression between the blood fractions, the expression levels were scaled to the amount of whole blood required. This clearly indicates the difference in determining hsa-miR-423-5p expression in plasma samples free or substantially free of blood cells or platelets (PPP: level=244) in comparison to plasma samples not free or not substantially free of blood cells or platelets (PRP: level=1252).

The Examples are designed in order to further illustrate the present invention and serve a better understanding. They are not to be construed as limiting the scope of the invention in any way.

Example 1: Microarray-Based Determination of Expression Profiles

The RNA-samples of HF-patients (HF-REF=non-ischaemic heart failure with reduced ejection fraction) and healthy controls were analyzed employing microarray hybridization on the Geniom Realtime Analyzer (febit biomed GmbH, Heidelberg, Germany) using the Geniom Biochip miRNA *Homo sapiens*. Each microfluidic microarray contains complementary dna-probes of 866 miRNAs and miRNA* (each represented by 7 replicates) as annotated in the Sanger miRBase 12.0. Sample labeling with biotin has been carried out by enzymatic on-chip labeling of miRNAs employing the MPEA-assay (Vorwerk et. al. N Biotechnol. 2008, 25(2-3):142-9). Following hybridization for 16 hours at 42° C. the biochip was washed automatically and a program for signal enhancement was processed with the Geniom Realtime Analyzer. The resulting detection pictures were evaluated using the Geniom Wizard Software. For each array, the median signal intensity was extracted from the raw data file such that for each miRNA seven intensity values have been calculated corresponding to each replicate copy of miRBase on the array. Following background correction, the seven replicate intensity values of each miRNA were summarized by their median value. To normalize the data across different arrays, quantile normalization was applied and all further analyses were carried out using the normalized and background subtracted intensity values, including statistical analysis and data filtering.

Example 2: Preparation of Plasma Sample that is Free of or Substantially Free of Blood Cells or Platelets (and Microvesicles)

5.1 Blood Draw

For platelet-preparations derived from whole blood, venous blood is conveniently drawn into EDTA-tubes (7.5 ml S-Monovette, Sarstedt/10 ml, Vaccutainer, BD Heidelberg, Germany), Na-citrate tubes (380%; 4.5 ml Vaccutainer, BD Heidelberg, Germany) or ACD-tubes (ACD type A, 8.5 ml, ACD type B, 6.5 ml Vaccutainer, BD Heidelberg, Germany).

5.2 Preparation of Platelet-Rich-Plasma (PRP)

Freshly collected whole blood is centrifuged with soft spin (170 g, 15 min) to make Platelet-Rich-Plasma (PRP, top-layer), buffy coat (white blood cells, middle layer) and red blood cells (bottom layer), from which the PRP is collected by careful pipetting off the top layer, taking care not to harm the buffy-coat layer.

5.3 Preparation of Platelet-Poor-Plasma (PPP)

Platelet-poor-plasma (PPP) is obtained from PRP by a second hard spin centrifugation (5000 g, 3 min) step, where remaining blood cells or platelets are pelleted out of the plasma to yield platelet-concentrate as a pellet at the bottom of the tube and platelet-poor-plasma (PPP) as the supernatant.

---

The invention claimed is:

1. A method for diagnosing heart failure in a subject comprising the steps of:
   (i) providing a whole blood sample obtained from a subject,
   (ii) centrifuging the whole blood sample at a centrifugation speed of between 170 g and 600 g for at least 10 minutes, thereby separating the whole blood sample into a red blood cell fraction, buffy coat and a platelet-rich plasma sample,
   (iii) centrifuging the platelet-rich plasma sample at a centrifugation speed of between 3000 g and 5000 g for at least 3 minutes, thereby separating the platelet-rich plasma sample into a pellet and a platelet-poor plasma sample,
   (iv) determining an expression profile of hsa-miR-423-5p in the platelet-poor plasma sample, and
   (v) comparing said expression profile to a reference, wherein said comparison allows to determine whether the subject suffers from heart failure,
wherein the platelet-poor plasma sample comprises less than 10,000 blood cells per microliter.

2. The method according to claim 1, wherein the platelet-poor plasma sample is free of red blood cells, white blood cells and platelets.

3. The method according to claim 1, wherein the platelet-poor plasma sample is free of hsa-miR-423-5p expressed in red blood cells, white blood cells and platelets.

4. The method according to claim 1, wherein the determination of the expression profile in step (iv) comprises the steps of:
   (a) isolating total RNA from said platelet-poor plasma sample,
   (b) transcribing the total RNA into cDNA,
   (c) optionally amplifying said cDNA, and
   (d) determining an expression profile of hsa-miR-423-5p from the cDNA-transcript(s) of step (b) or (c).

5. The method according to claim 1, wherein a kit is used in said method, said kit comprising:
   (a) polynucleotide primer(s), polynucleotide probe(s), and/or polynucleotide adapter(s) for determining an expression profile of hsa-miR-423-5p in a platelet-poor plasma sample,
   (b) a reference,
   (c) optionally a data carrier, and
   (d) optionally a whole blood collection tube.

6. The method according to claim 5, wherein said polynucleotide primer(s), polynucleotide probe(s), and/or polynucleotide adapter(s) are for determining an expression profile by qRT-PCR, comprising primers or adapters comprising one or more selected from stem-loop reverse primer X-AAAGTCTC where X is 5'-CTCAACTGGTGTCGTGGAGTCGGCAATTCAGTTGAG (SEQ ID NO:3), forward primer Y-TGAGGGGCAGAGAGCGA (SEQ ID NO:2) where Y is 5'-ACACTCCAGCTGGG (SEQ ID NO:4), reverse primer Z where Z is 5'-CTCAACTGGTGTCGTGGAGT (SEQ ID NO:5), dual-labeled probe 56-FAM-P-AAAGTCTC-3IABLFQ where 56-FAM is 5' 6-FAM (Fluorescein) and 3IABLFQ is Iowa black fluorescein quencher and P is 5'-TTCAGTTGAG (SEQ ID NO:6), forward primer GGGCAGAGAGCGAGAC (SEQ ID NO:7) and reverse primer GGTCCAGTTTTTTTTTTTTTTAAAGTC (SEQ ID NO:8).

7. The method according to claim 5, wherein said polynucleotide primer(s), polynucleotide probe(s), and/or polynucleotide adapter(s) are for determining an expression profile by next generation sequencing, comprising primers or adapters comprising one or more selected from the group consisting of:
   P-UCGUAUGCCGUCUUCUGCUUGUidT (SEQ ID NO:10);
   5'/5rApp/ATCTCGTATGCCGTCTTCTGCTTG/3ddC/ (SEQ ID NO:12);
   GUUCAGAGUUCUACAGUCCGACGAUC (SEQ ID NO:13);
   CAAGCAGAAGACGGCATACGA (SEQ ID NO:14);
   5'GCCTTGGCACCCGAGAATTCCA (SEQ ID NO:15);
   CAAGCAGAAGACGGCATACGAGATCGTGATGTGACTGGAGTTCCTTGGCACCCGAGAATTCCA (SEQ ID NO:16);
   AATGATACGGCGACCACCGACAGGTTCAGAGTTCTACAGTCCGA (SEQ ID NO:17); and
   AATGATACGGCGACCACCGAGATCTACACGTTCAGAGTTCTACAGTCCGA (SEQ ID NO:18).

8. The method according to claim 1, wherein the platelet-poor plasma sample comprises less than 10.000 platelets per microliter.

9. The method according to claim 1, wherein the method further comprises the step of administering a therapy to the subject suffering from heart failure.

10. The method according to claim 1, wherein the reference is derived from expression profiles determined from hsa-miR-423-5p in a platelet-poor plasma sample of healthy controls.

11. The method according to claim 10, wherein an up-regulation of hsa-miR-423-5p in a platelet-poor plasma sample of the subject compared to the reference indicates that the subject suffers from heart failure.

12. A method for determining an expression profile of a set of miRNAs comprising at least hsa-miR-423-5p comprising the steps of:
   (i) providing a whole blood sample comprising hsa-miR-423-5p of a subject,
   (ii) centrifuging said whole blood sample at a centrifugation speed of between 170 g and 600 g for at least 10 minutes, thereby separating the whole blood sample into a red blood cell fraction, buffy coat fraction and a platelet-rich plasma sample,
   (iii) centrifuging the platelet-rich plasma sample at a centrifugation speed of between 3000 g and 5000 g for at least 3 minutes, thereby separating the platelet-rich plasma sample into a pellet and a platelet-poor plasma sample, and
   (iv) determining an expression profile of hsa-miR-423-5p in the platelet-poor plasma sample,
wherein the platelet-poor plasma sample comprises less than 10,000 blood cells per microliter.

13. The method of claim 1, wherein step (ii) is carried out at a centrifugation speed of 170 g for 15 minutes and step (iii) is carried out at a centrifugation speed of 5000 g for 3 minutes.

14. The method of claim 1, wherein step (ii) is carried out at a centrifugation speed of 600 g for 10 minutes and step (iii) is carried out at a centrifugation speed of 3000 g for 10 minutes.

15. The method of claim 12, wherein step (ii) is carried out at a centrifugation speed of 170 g for 15 minutes and step (iii) is carried out at a centrifugation speed of 5000 g for 3 minutes.

16. The method of claim 12, wherein step (ii) is carried out at a centrifugation speed of 600 g for 10 minutes and step (iii) is carried out at a centrifugation speed of 3000 g for 10 minutes.

\* \* \* \* \*

SEQUENCE LISTING

```
<160> NUMBER OF SEQ ID NOS: 18

<210> SEQ ID NO 1
<211> LENGTH: 23
<212> TYPE: RNA
<213> ORGANISM: Homo sapiens

<400> SEQUENCE: 1
ugaggggcag agagcgagac uuu                                            23

<210> SEQ ID NO 2
<211> LENGTH: 17
<212> TYPE: DNA
<213> ORGANISM: Artificial Sequence
<220> FEATURE:
<223> OTHER INFORMATION: Synthetic primer

<400> SEQUENCE: 2
tgaggggcag agagcga                                                   17

<210> SEQ ID NO 3
<211> LENGTH: 36
<212> TYPE: DNA
<213> ORGANISM: Artificial Sequence
<220> FEATURE:
<223> OTHER INFORMATION: Synthetic primer

<400> SEQUENCE: 3
ctcaactggt gtcgtggagt cggcaattca gttgag                              36

<210> SEQ ID NO 4
<211> LENGTH: 14
<212> TYPE: DNA
<213> ORGANISM: Artificial Sequence
<220> FEATURE:
<223> OTHER INFORMATION: Synthetic primer

<400> SEQUENCE: 4
acactccagc tggg                                                      14

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
ctcaactggt gtcgtggagt                                                20

<210> SEQ ID NO 6
<211> LENGTH: 10
<212> TYPE: DNA
<213> ORGANISM: Artificial Sequence
<220> FEATURE:
<223> OTHER INFORMATION: Synthetic Probe

<400> SEQUENCE: 6
```
ttcagttgag                                                              10

<210> SEQ ID NO 7
<211> LENGTH: 16
<212> TYPE: DNA
<213> ORGANISM: Artificial Sequence
<220> FEATURE:
<223> OTHER INFORMATION: Synthetic primer

<400> SEQUENCE: 7
gggcagagag cgagac                                                       16

<210> SEQ ID NO 8
<211> LENGTH: 28
<212> TYPE: DNA
<213> ORGANISM: Artificial Sequence
<220> FEATURE:
<223> OTHER INFORMATION: Synthetic primer

<400> SEQUENCE: 8
ggtccagttt tttttttttt ttaaagtc                                          28

<210> SEQ ID NO 9
<211> LENGTH: 21
<212> TYPE: DNA
<213> ORGANISM: Artificial Sequence
<220> FEATURE:
<223> OTHER INFORMATION: Synthetic adapter for forming RNA-DNA hybrids

<400> SEQUENCE: 9
tggaattctc gggtgccaag g                                                 21

<210> SEQ ID NO 10
<211> LENGTH: 22
<212> TYPE: RNA
<213> ORGANISM: Artificial Sequence
<220> FEATURE:
<223> OTHER INFORMATION: Synthetic adapter for foming RNA-DNA hybrid

<400> SEQUENCE: 10
ucguaugccg ucuucugcuu gu                                                22

<210> SEQ ID NO 11
<211> LENGTH: 18
<212> TYPE: DNA
<213> ORGANISM: Artificial Sequence
<220> FEATURE:
<223> OTHER INFORMATION: Synthetic adapter for forming RNA-DNA hybrid
<220> FEATURE:
<221> NAME/KEY: misc_feature
<222> LOCATION: (18)..(18)
<223> OTHER INFORMATION: di-deoxy

<400> SEQUENCE: 11
ctgtaggcac catcaatc                                                     18

<210> SEQ ID NO 12
<211> LENGTH: 25
<212> TYPE: DNA
<213> ORGANISM: Artificial Sequence
<220> FEATURE:
<223> OTHER INFORMATION: Synthetic adapter for forming RNA-DNA hybrid
<220> FEATURE:
<221> NAME/KEY: misc_feature
<222> LOCATION: (25)..(25)
<223> OTHER INFORMATION: di-deoxy

<400> SEQUENCE: 12
atctcgtatg ccgtcttctg cttgc                                    25

<210> SEQ ID NO 13
<211> LENGTH: 26
<212> TYPE: RNA
<213> ORGANISM: Artificial Sequence
<220> FEATURE:
<223> OTHER INFORMATION: Synthetic 5' RNA adapter

<400> SEQUENCE: 13
guucagaguu cuacaguccg acgauc                                   26

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
caagcagaag acggcatacg a                                        21

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
gccttggcac ccgagaattc ca                                       22

<210> SEQ ID NO 16
<211> LENGTH: 63
<212> TYPE: DNA
<213> ORGANISM: Artificial Sequence
<220> FEATURE:
<223> OTHER INFORMATION: Synthetic primer

<400> SEQUENCE: 16
caagcagaag acggcatacg agatcgtgat gtgactggag ttccttggca cccgagaatt    60
cca                                                                 63

<210> SEQ ID NO 17
<211> LENGTH: 44
<212> TYPE: DNA
<213> ORGANISM: Artificial Sequence
<220> FEATURE:
<223> OTHER INFORMATION: Synthetic primer

<400> SEQUENCE: 17
aatgatacgg cgaccaccga caggttcaga gttctacagt ccga                    44

<210> SEQ ID NO 18
<211> LENGTH: 50
<212> TYPE: DNA
<213> ORGANISM: Artificial Sequence
<220> FEATURE:
<223> OTHER INFORMATION: Synthetic primer

<400> SEQUENCE: 18
aatgatacgg cgaccaccga gatctacacg ttcagagttc tacagtccga              50